United States Patent [19]

Lagow et al.

[11] Patent Number: 4,570,004

[45] Date of Patent: Feb. 11, 1986

[54] PERFLUORO CROWN ETHERS

[75] Inventors: Richard J. Lagow; Wen-Huey Lin, both of Austin, Tex.

[73] Assignee: The Board of Regents, University of Texas System, Austin, Tex.

[21] Appl. No.: 597,759

[22] Filed: Apr. 6, 1984

[51] Int. Cl.[4] ............................................ C07D 323/00
[52] U.S. Cl. ..................................... 549/352; 549/353
[58] Field of Search ................................. 549/352, 353

[56] References Cited

U.S. PATENT DOCUMENTS 3,632,606  1/1972  Talbott ................................ 260/338
4,113,772  9/1978  Lagow ................................. 562/583
4,281,119  7/1981  Lagow ................................. 544/106

FOREIGN PATENT DOCUMENTS 1294657  11/1972  United Kingdom .

OTHER PUBLICATIONS

G. Gokel, et al, "Principles and Synthetic Applications in Crown Ether Chemistry", 168–184 (1976).

J. Adcock, et al, "Successful Direct Fluorination of Oxygen–Containing Hydrocarbons," 40 J. Org. Chem. 3271 (1975).

J. Adcock, et al, "Synthesis of Perfluoro-1, 4-dioxane, Perfluro (ethyl acetate), and Perfluoropivaloyl Fluoride by Direct Fluorination," 96 J. Amer. Chem. Soc. 7588 (1974).

R. Lagow, et al, "Direct Fluorination: A 'New' Approach to Fluorine Chemistry," 26 Progress in Inorganic Chemistry 161 (1979).

*Primary Examiner*—C. Warren Ivy
*Attorney, Agent, or Firm*—Arnold, White & Durkee

[57] ABSTRACT

This specification discloses novel perfluorinated crown ethers which are believed useful as oxygen carriers and in the construction of various biomedical products.

5 Claims, No Drawings

PERFLUORO CROWN ETHERS

Some of the work described in this patent was funded by the Air Force Office of Scientific Research, Grant Nos. AFOSR-78-3658 and AFOSR-82-0197.

BACKGROUND OF THE INVENTION

The present invention relates to perfluorinated cyclic ethers and methods of synthesizing them.

"Crown" ethers can be generally defined as macroheterocyclic compounds comprising the repeating unit (—O—$CH_2$—$CH_2$—). As explained in "Principles and Synthetic Applications in Crown Ether Chemistry," Gokel and Durst, Synthesis 168–184 (1976), which is incorporated in this specification by reference, the name "crown" comes from the appearance of the space filling (CPK) molecular models and the ability of these compounds to "crown" cations by complexation. For example, 15-crown-5 ether can be represented as follows:

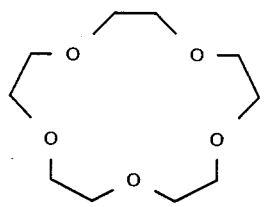

Direct fluorination of crown ethers, or any other compound, has presented difficult kinetic and thermodynamic problems in the past. Directly fluorinated crown ethers are unknown because conventional synthesis methods are not available. The highly exothermic nature of direct fluorination reactions has had explosive results in some cases, and has caused many researchers to avoid these reactions altogether.

A different approach, often referred to as the "La-Mar" direct fluorination process, was developed to overcome these problems. The La-Mar process generally involves blanketing material to be fluorinated in an inert atmosphere. Fluorine gas, or halogen fluorides, are then introduced. This fluorine-containing gas may be introduced into the reaction area by itself or in combination with an inert gas. In either case, the initial concentration of fluorine containing gas is kept low to prevent the reaction from occurring too rapidly, which would cause decomposition of the product, as well as the other problems of prior art direct fluorinations reactions.

As the reaction proceeds, the fluorine or halogen fluoride concentration can be safely increased, because as the reactant molecules become more highly fluorinated, they are able to withstand more fluorine collisions without decomposing. The specific dilution scheme used for the reaction gas depends on the specific reactant, desired product, and other variables.

The perfluorinated analogs of crown ethers are one group of compounds that have not been synthesized before. These ethers have been synthetically inaccessible by conventional reactions of fluorocarbons, and are apparently not capable of synthesis by fluorination on selective fluorination reagents. Because they have not been made previously, there has been no study of the potential uses such compounds might have.

SUMMARY OF THE INVENTION

Perfluorinated crown ethers in accordance with the present invention comprise the repeating unit (—O—$CF_2$—$CF_2$—)$_n$, where n is at least 3. Compounds where n is between 3 and 7 appear to be especially good candidates for the uses discussed below.

Perfluorinated crown ethers can be synthesized by first establishing a substantially inert atmosphere around a crown ether, introducing into the substantially inert atmosphere a reaction gas stream which includes an inert gas, and a gas selected from the group consisting of fluorine, halogen fluorides, and fluorine-halogen fluoride mixtures, the initial non-inert concentration of the reaction gas stream being no more than about 6% by volume, and controlling the temperature between approximately −80° and 60° C. until the reaction is terminated.

These perfluorinated compounds generally exhibit different properties than their hydrocarbon analogs. They are believed to be unusually stable, and therefore less subject to chemical attack or thermal degradation. In addition, they are more volatile and less basic than the corresponding hydrocarbons. Structural information obtained from single crystals of perfluorinated crown ethers indicates that the ring is "puckered" in a way that causes the oxygen atoms to be projected toward a metal coordination site, suggesting that these compounds will be useful as ligands for metals and organometallic species.

Perfluorinated crown ethers are also believed useful as oxygen carriers, and for other biomedical purposes. One example is the coordination of toxic metals in the bloodstream. In contrast to hydrocarbon crown ethers, the fluorocarbon analogs are compatible with blood and vascular tissue. They are also non-thrombrogenic.

DETAILED DESCRIPTION OF SPECIFIC EMBODIMENTS

Perfluorinated crown ethers in accordance with the present invention are generally synthesized by contacting their hydrocarbon analogs with a gas mixture containing an inert gas and either fluorine, halogen fluorides or fluorine-halogen fluoride mixtures. The percentage of fluorine and halogen fluoride in the mixture must initially be kept low to prevent decomposition. This is typically accomplished by first establishing an inert atmosphere in the reaction vessel, and then introducing a low flow rate of fluorine or halogen fluoride gas, either by itself, or mixed with an inert gas. If this reaction gas stream contains both inert and fluorine (and/or halogen fluorides), the noninert component will usually be no more than about 6% by volume of the total flow rate.

The exact dilution conditions will vary depending on the reactants, desired product, and the like. The reaction temperature will also vary depending on those factors, but it will generally be between −80° C. and 60° C. Both the fluorine concentration and the reaction temperature will usually be increased as the reaction progresses.

Apparatus for the reaction can suitably include sources of fluorine and helium, flow measuring means for both the fluorine and helium, and needle valves to control the fluorine and helium flow rates, a brass mixing chamber packed with fine copper turnings to mix the fluorine and helium, a reaction chamber, an alumina-packed cylinder to receive gas exiting the reaction chamber and dispose of unreacted fluorine, and a gas outlet. In the examples that follow, the fluorine flow was measured by Hasting-Raydist model LF-50 mass flow meter and model F-50M transducer, and the helium flow rate was measured by a simple gas flow meter. The reaction chamber was a 18 inch by 1.5 inch nickel tube containing a prefluorinated nickel boat, 7.5 inches long and 0.75 inch wide, in which the solid reactant was placed.

To eliminate back diffusion of oxygen from the alumina packed cylinder, a T-joint was placed between it and the reaction vessel, and a constant flow of nitrogen was introduced through that joint to continually flush the fluorine through an alumina trap without back diffusion. A nitrogen gas bubbler was placed in the line below the alumina packed cylinder to prevent air and moisture from entering the system.

It is extremely important to remove all sources of oxygen and water from the system. Free oxygen can cause cross-linking of the reactant, and can form carbonyl groups such as acid fluorides and peroxides. Crosslinking will greatly decrease the yield of perfluoro crown ethers.

Additional information on the reaction and apparatus are given in U.S. Pat. No. 4,281,119, and "Direct Fluorination: A 'New' Approach to Fluorine Chemistry," R. Lagow and J. Margrave, 26 Progress in Inorganic Chemistry, 161–210 (1979). Both of those documents are incorporated in this specification by reference.

Several factors influence the yield of perfluorinated crown ether: the surface area exposed to fluorine, the reaction temperature, the reaction time, and other fluorination conditions. The surface area variable appears to be especially important. One way of maximizing the surface area is to coat the starting crown ether on a solid sodium fluoride support. Sodium fluoride will serve the additional purpose of reacting with the hydrogen fluoride generated by the reaction.

The following examples give additional details about the reaction and products.

EXAMPLE 1

Eighteen-crown-6 ether was purified by recrystallization. Eighty-one one-hundredths of a gram of 18-crown-6 and 2.09 grams of sodium fluoride were ground to a fine powder and mixed well in a dry box. This mixture was placed in a nickel boat and loaded in the reactor. A $-78°$ C. trap was placed downstream of the reactor to collect volatile products.

A helium purge was maintained for several hours before fluorine gas was introduced. The gas flow rates and reactor temperatures are shown in Table 1.

TABLE 1

| Total Time (hrs) | Incremental Time (hrs) | He (cc/min) | $F_2$ (cc/min) | Temp. (°C.) |
|---|---|---|---|---|
| 16 | 16 | 60 | 0 | −78 |
| 39 | 23 | 40 | 1.0 | −78 |
| 63 | 24 | 20 | 1.0 | −78 |
| 87 | 24 | 10 | 1.0 | −78 |
| 111 | 24 | 10 | 3.0 | −78 |
| 135 | 24 | 0 | 1.0 | −78 |
| 171 | 36 | 0 | 2.0 | −78 |
| 200 | 29 | 0 | 2.0 | room temp. |
| 224 | 24 | 0 | 2.0 | 45 |
| 271 | 47 | 0 | 2.0 | 60 |
| 295 | 24 | 60 | 0 | 60 |

The volatile products were transferred from the $-78°$ C. trap to a vacuum line for fractionation. A fraction was obtained that stopped at $-23°$ C. The $-23°$ fraction was further separated using a gas chromotograph with a fluorosilicone column.

The major component of the product was identified as perfluoro 18-crown-6.

Its yield was 33.5% (0.715 grams) based on starting 18-crown-6. It was a volatile, colorless, crystalline solid, which could be easily sublimed. Elemental analysis was consistent with the formula of $C_{12}F_{24}O_6$ (calculated: 20.71% C, 65.50% F; found: 20.90% C, 65.35% F). The vapor phase IR spectrum exhibited bands at 1210(vs), 1140(vs) and 725(sh) cm$^{-1}$. The $^{19}$F NMR ($C_6F_6$ solution) contained a singlet at −91.0 ppm from external $CFCl_3$. The $^{13}$C NMR ($C_6F_6$ solution) also contained a singlet which was observed at 114.9 ppm from external TMS. The mass spectrum (with the spectrometer cooled to ambient temperature) gave no parent peak but m/e of 677 was observed which corresponded to the molecular ion minus one fluorine. The remaining components from the GC separation were identified mainly as $CF_3O(CF_2CF_2O)_4CF_3$ (40 mg) and $CF_3CF_2O(CF_2CF_2O)_4CF_3$ (22 mg). These reaction by-products resulted from the fragmentation of the ring system to produce the straight chain perfluoro polyethers.

EXAMPLE 2

Perfluoro 15-crown-5 was synthesized using procedures generally the same as in Example 1. The reaction parameters are listed in Table 2.

TABLE 2

| Total Time (hrs) | Incremental Time (hrs) | He (cc/min) | $F_2$ (cc/min) | Temp. (°C.) |
|---|---|---|---|---|
| 18 | 18 | 60 | 0 | −78 |
| 43 | 25 | 40 | 1.0 | −78 |
| 67 | 24 | 20 | 1.0 | −78 |
| 91 | 24 | 10 | 1.0 | −78 |
| 120 | 29 | 10 | 3.0 | −78 |
| 160 | 40 | 0 | 1.0 | −78 |
| 203 | 43 | 0 | 2.0 | −78 |
| 232 | 29 | 0 | 2.0 | room temp. |
| 256 | 24 | 0 | 2.0 | 45 |
| 280 | 24 | 60 | 0 | 45 |

The properties and characterization of the perfluoro 15-crown-5 product are given in Table 3.

TABLE 3

| | |
|---|---|
| Boiling Point, °C. | 146° |
| Elemental Analysis | $C_{10}F_{20}O_5$ |
| Calcd. | % C, 20.71; % F, 65.50 |
| Found | % C, 20.90; % F, 65.04 |
| IR (vapor phase) cm$^{-1}$ | 1380(w), 1180(vs, br), 800(w), 730(w) |
| NMR (neat liquid) | $^{19}$F - singlet, −91.8 ppm (ext. $CFCl_3$) $^{13}$C - singlet, 114.9 ppm (ext. TMS) |
| Mass Spectrum, m/e | 580 ($C_{10}F_{20}O_5$, P) |

EXAMPLE 3

Perfluoro 12-crown-4 was synthesized using generally the same procedures described in Examples 1 and 2. The reaction parameters are listed in Table 4.

TABLE 4

| Total Time (hrs) | Incremental Time (hrs) | He (cc/min) | $F_2$ (cc/min) | Temp. (°C.) |
| --- | --- | --- | --- | --- |
| 20 | 20 | 60 | 0 | −78 |
| 42 | 22 | 40 | 1.0 | −78 |
| 67 | 25 | 20 | 1.0 | −78 |
| 91 | 24 | 10 | 1.0 | −78 |
| 115 | 24 | 10 | 3.0 | −78 |
| 148 | 33 | 0 | 1.0 | −78 |
| 185 | 37 | 0 | 2.0 | −78 |
| 209 | 24 | 0 | 2.0 | room temp. |
| 236 | 27 | 0 | 2.0 | 45 |
| 260 | 24 | 60 | 0 | 45 |

The properties and characterization of perfluoro 12-crown-4 product are given in Table 5.

TABLE 5

| Boiling Point, °C. | 118° |
| --- | --- |
| Elemental Analysis | $C_8F_{16}O_4$ |
| Calcd. | % C, 20.71; % F, 65.50 |
| Found | % C, 20.99; % F, 65.18 |
| IR (vapor phase) cm$^{-1}$ | 1365(w), 1262(vs,sh), 1120(m), 1080(m), 820(w), 745(w) |
| NMR (heat liquid) | $^{19}F$ - singlet, −90.0 ppm (ext. $CFCl_3$) $^{13}C$ - singlet 114.9 ppm (ext. TMS) |
| Mass Spectrum, m/e | 445 ($C_8F_{15}O_4$, P-F) |

Table 6 shows the straight chain fragmentation products of the reaction, along with mass spectral and $^{19}F$ NMR data for them.

TABLE 6

| Compound (highest m/e in mass spec) | Assigned $^{19}F$ Chemical Shift in ppm (vs. Ext. $CFCl_3$) | Relative Intensities Obs. | Relative Intensities Theor. |
| --- | --- | --- | --- |
| 1. $CF_3OCF_2CF_2OCF_2CF_2OCF_3$<br>    a   b   c   c   b   a<br>367 ($C_6F_{13}O_3$, P—F) | a = −58.5<br>b = −93.2<br>c = −91.1 | 1.5<br>1.1<br>1.0 | 1.5<br>1.0<br>1.0 |
| 2. $CF_3CF_2OCF_2CF_2OCF_2CF_2OCF_3$<br>    a  b   c   c   c   c   d<br>417 ($C_7F_{15}O_3$, P—F) | a = −89.7<br>b = −93.0<br>c = −91.0<br>d = −58.3 | 1.5<br>1.0<br>4.4<br>1.4 | 1.5<br>1.0<br>4.0<br>1.5 |
| 3. $CF_3CF_2OCF_2CF_2OCF_2CF_2OCF_2CF_3$<br>    a  b   b   b   b   b   a<br>467 ($C_8F_{17}O_3$, P—F) | a = −89.9<br>b = −91.0 | 1.0<br>2.1 | 1.0<br>2.0 |
| 4. $CF_3O[CF_2CF_2OCF_2CF_2OCF_2CF_2O]CF_3$<br>    a   b   c   c   c   b   a<br>483 ($C_8F_{17}O_4$, P—F) | a = −58.1<br>b = −92.0<br>c = −90.9 | 1.5<br>1.0<br>2.2 | 1.5<br>1.0<br>2.0 |
| 5. $CF_3CF_2O[CF_2CF_2OCF_2CF_2OCF_2CF_2O]CF_3$<br>    a  b   c   c   c   c   c   d<br>533 ($C_9F_{19}O_3$, P—F) | a = −89.6<br>b = −92.7<br>c = −90.8<br>d = −58.0 | 1.2<br>1.0<br>5.2<br>1.2 | 1.5<br>1.0<br>6.0<br>1.5 |
| 6. $CF_3O[CF_2CF_2OCF_2CF_2OCF_2CF_2OCF_2CF_2O]CF_3$<br>    a   b   c   c   c   c   c   b   a<br>599 ($C_{10}F_{21}O_5$, P—F) | a = −58.3<br>b = −93.0<br>c = −91.0 | 1.5<br>1.0<br>2.9 | 1.5<br>1.0<br>3.0 |
| 7. $CF_3CF_2O[CF_2CF_2OCF_2CF_2OCF_2CF_2OCF_2CF_2O]CF_3$<br>    a  b   c   c   c   c   c   c   c   d<br>599 ($C_{10}F_{21}O_5$, P—$CF_3$) | a = −89.4<br>b = −92.7<br>c = −90.6<br>d = −58.0 | 1.3<br>1.0<br>8.0<br>1.4 | 1.5<br>1.0<br>8.0<br>1.5 |

The crown ethers used to synthesize the compounds of the present invention are commercially available. Twelve-crown-4, 15-crown-5, and 18-crown-6 are all available from either Alfa Products of Danvers, Mass., or Aldrich Chemical Company of Milwaukee, Wis.

The proceeding description is intended to illustrate the present invention, not to provide an exhaustive list of all possible embodiments.

We claim:

1. Perfluorinated crown ethers comprising the repeating unit $(-O-CF_2-CF_2-)_n$, where n is at least 3.

2. The perfluorinated crown ethers of claim 1, where n is between 3 and 7, inclusive.

3. Perfluoro 12-crown-4 ether.

4. Perfluoro 15-crown-5 ether.

5. Perfluoro 18-crown-6 ether.

* * * * *